United States Patent
Ragnarsdottir et al.

(10) Patent No.: US 9,649,072 B2
(45) Date of Patent: May 16, 2017

(54) DEVICE FOR MEASURING SPINAL MOBILITY

(75) Inventors: Maria Ragnarsdottir, Kopavogur (IS);
Geir Gudmundsson, Kopavogur (IS);
Jon Matthiasson, Reykjavik (IS);
Halldor Kristinsson, Reykjavik (IS);
Gisli Sverrisson, Reykjavik (IS)

(73) Assignees: MTT EHF, Reykjavik (IS); Maria Ragnarsdottir, Kopavogur (IS)

( * ) Notice: Subject to any disclaimer, the term of this patent is extended or adjusted under 35 U.S.C. 154(b) by 565 days.

(21) Appl. No.: 14/118,186

(22) PCT Filed: May 18, 2012

(86) PCT No.: PCT/IS2012/050008
§ 371 (c)(1),
(2), (4) Date: Feb. 24, 2014

(87) PCT Pub. No.: WO2012/157000
PCT Pub. Date: Nov. 22, 2012

(65) Prior Publication Data
US 2014/0188008 A1    Jul. 3, 2014

(30) Foreign Application Priority Data
May 17, 2011 (SI) .............................. 8955

(51) Int. Cl.
A61B 5/11    (2006.01)
A61B 5/00    (2006.01)
A61B 5/103   (2006.01)

(52) U.S. Cl.
CPC ............ *A61B 5/742* (2013.01); *A61B 5/103* (2013.01); *A61B 5/11* (2013.01); *A61B 5/1126* (2013.01); *A61B 5/4566* (2013.01); *A61B 2562/0252* (2013.01)

(58) Field of Classification Search
CPC . A61F 2/442; A61F 2220/0025; A61F 2/4611
See application file for complete search history.

(56) References Cited

U.S. PATENT DOCUMENTS

| 4,583,555 A | 4/1986 | Malcom et al. |
| 4,762,134 A | 8/1988 | Gala |

(Continued)

FOREIGN PATENT DOCUMENTS

| DE | 10 2004 021 446 A1 | 11/2005 |
| WO | WO 96/22051 | 7/1996 |

*Primary Examiner* — Adam J Eiseman
*Assistant Examiner* — Patrick Fernandes
(74) *Attorney, Agent, or Firm* — Muncy, Geissler, Olds & Lowe, P.C.

(57) ABSTRACT

A device and method for measurement of spinal mobility are provided for measuring spinal mobility. The apparatus is a hand-held device that includes a gripping portion connected to a force transmitter, a reference member, displacement sensor, and load cell. A force applied downwardly on the gripping portion is transmitted to the force transmitter which is placed on a vertebra of the spine of a subject. The reference member rests on an adjacent vertebra. The displacement sensor determines displacement of the force transmitter relative to the reference member, as a function of the applied force measure by the load cell.

4 Claims, 13 Drawing Sheets

(56) References Cited

U.S. PATENT DOCUMENTS

| | | | |
|---|---|---|---|
| 5,441,413 A * | 8/1995 | Kumar | G09B 23/28 |
| | | | 434/262 |
| 5,911,695 A | 6/1999 | Watkins et al. | |
| 6,539,328 B1 * | 3/2003 | Cremonese | A61B 5/103 |
| | | | 702/151 |

* cited by examiner

DEVICE FOR MEASURING SPINAL MOBILITY

FIELD OF INVENTION

The present invention relates to a device and a method for providing consistent and reproducible measurements of spinal mobility.

BACKGROUND OF INVENTION

Spinal mobility has for a long time been determined using manual methods, where the practitioner would press down on one or more vertebra to be analyzed. Such methods are subjective, as the practitioner would try to move the vertebra to be tested with his/her fingers or hand and make an observation based on how much mobility he/she could detect. The practitioner would than make a record of his observation, which is not referenced to any standard, and comparison over a period of time would be very difficult and inaccurate.

Devices have been suggested in order to measure spinal mobility objectively. U.S. Pat. No. 6,539,328 discloses a device comprising an impulse and sensing head, which determines spinal segment mobility by applying a force impulse at an angle of incidence to a spinal segment and generating a wave form characteristic of spinal mobility. An inclinometer determines the angle of incidence of contact with the spinal segment in one or more axis. The device collects data signals from the inclinometer and the head in such a manner that a signal corresponding to the angle of incidence at the same time will be captured by the data acquisition circuitry. This patent document also describes earlier prior art devices based on piezoelectric sensors and measurements of electronic waveforms reflecting the resistance of a spinal segment under pressure. These devices have however not been used commercially and there is a clear need for alternative, simple and accurate devices for measuring spinal mobility.

SUMMARY OF INVENTION

The present invention provides a device and a method for measuring spinal mobility. A hand-held device is provided which is ergonomically easy to use and comprises necessary operational components to be used by a practitioner, such as a physiotherapist, to measure the spinal mobility of a patient in a much less subjective manner than with traditional manual methods. The function of the invention can be explained as follows: it will require a certain force to move a vertebra in relation to an adjacent vertebra, this force depends on the spinal mobility of the person, i.e., the degree of spinal mobility determines how easily one vertebra can be displaced relative to the adjacent vertebra. The device of the invention measures the displacement of a vertebra as a function of applied force and thus provides a measurement of the spinal mobility.

The invention provides in a main aspect a hand-held device, wherein the device comprises a support frame, for resting on the back of a subject to be measured, a gripping portion, engaged to the support frame, a force transmitter, a reference member, a reference displacement sensor, a load cell, and an electrical power source.

The force transmitter is connected to the gripping portion, such that a force applied downwardly on the gripping portion is transferred to the force transmitter, wherein the load cell is connected to said force transmitter to quantitatively detect the force applied to said force transmitter. The frame comprises a reference member in proximity to the force transmitter, such that when the device is placed on the back/spine of said subject such that the force transmitter is positioned on a first vertebra, the reference member rests on a an adjacent vertebra. The reference displacement sensor is configured to measure displacement of the force transmitter relative to the reference member, thus the device measures displacement of the force transmitter as a function of the applied force to provide a measurement of spinal mobility. The reference member can be either rigidly joined to the frame or slidably connected thereto, as further described herein. In this regard, it should be noted that when displacement of the force transmitter is referred to, it is specifically the displacement of the distal surface end of the force transmitter that rest on the first vertebra, that is relevant. In certain embodiment the force transmitter has a soft end portion to soften the impact for patient comfort, where the soft end portion is compressed under pressure. In such embodiments, as further described below, it is of key importance that the displacement of the force transmitter distal surface be determined, in order to accurately determine the relative displacement of the vertebra on which the force transmitter rests.

The inner components of the device can be suitably held in a housing connected to or forming part of said frame. The housing is in some embodiments arranged to be slidably engaged with the gripping portion and the force transmitter, in such a way that force applied to the gripping portion is transmitted to the end of the force transmitter but substantially not to the frame and housing, i.e. it is essentially only the force transmitter that is pushed down on the vertebra, but not the support frame on the back of the subject.

In a second aspect, the present invention provides a method for measuring spinal tension/mobility. The method comprises the steps of placing a device on the spine of a subject, the device comprising a frame supporting a gripping means engaged with a force transmitter, a load cell, and a reference displacement sensor, such that the force transmitter is positioned on a first vertebra, Preferably the device used in the method is a device as further described herein above. The practitioner applies a vertical force (essentially perpendicular to the axis of the spine at that point) to the gripping means of the device and thereby a pressure/load to a first vertebra through the force transmitter, causing movement of the first vertebra relative to adjacent vertebra. This relative movement/displacement is measured with the reference displacement sensor. The reference displacement sensor is preferably arranged as described above, such that it measures directly the displacement of the force transmitter relative to a reference member. A movable reference member can also be used for the displacement measurement, resting on a second vertebra adjacent to the first vertebra, and moving in a frictionless fashion relative to the end of the force transmitter and this relative movement/displacement is registered.

Accordingly, the measurement gives a straight-forward two-point measurement of said relative movement as a function of the force applied to a vertebra, referred to as spinal mobility or vertebrae mobility. The device measures continuously or semi-continuously to obtain a series of datapoints x,y (force, displacement) as the gripping portion is pushed down, the series of points obtained provide a curve, of displacement of the measured vertebra as a function of applied force.

In an embodiment of the present invention the steps of applying force to the device and the step of measuring the relative movement of a first vertebra are repeated for two or more vertebra. Typically, the force on the device is applied manually, but is in certain embodiments applied by a mechanical linear force actuator,

DESCRIPTION OF THE PRESENT INVENTION

In the present context the term spinal mobility refers to the mobility (elasticity modulus) of one vertebra with respect to the next adjacent vertebrae in a spine of a subject.

A displacement sensor as used herein refers to sensor means which detect displacement of an object or point relative to another point.

The force transmitter is typically a rod or piston with a contact head that contacts the back of the subject, the force transmitter is connected to a load cell which is a transducer, which converts a force into an electrical signal. Atypical load cell comprises a strain gauge for converting the force into weak electrical signals, which are then amplified and the output of the transducer can suitably be converted by means of an algorithm in a central processing unit (cpu) to a value indicating the force applied to the transducer.

As mentioned above, the contact head can comprise a compressible soft end portion, to soften the impact on the vertebra. In such embodiments, the device is configured to accurately measure the displacement of the distal surface of the soft end portion of the contact head. This can suitably be accommodated with a sliding displacement member immediately adjacent to or embedded in the force transmitter soft end portion, which displacement member operates with the displacement sensor.

The functional elements of the device are preferably placed inside and/or attached to a housing attached to or merged with the frame. The housing can suitably enclose electronic components and further comprise an output screen, and can in some embodiments be configured to enclose a battery compartment.

The reference member can be configured in various different embodiments, all within the general scope of the invention. In one embodiment, the reference member is slidably connected to a carriage which is joined to the force transmitter and which carriage moves with the force transmitter when the force transmitter is pushed downwardly by a force applied on the gripping means. In this embodiment, the reference member is arranged to move slidably and essentially frictionless with respect to said carriage and the force transmitter. Thus, for making a measurement, the device is placed on the back of a subject such that the force transmitter rest on a selected vertebra and the reference member rest on an adjacent vertebra. Preferably, the distance between the force transmitter and reference member is adjustable to adjust for different distance between adjacent vertebra. When force is applied to the gripping portion and conducted through and towards the force transmitter, the force transmitter will dislocate the vertebra it pushes on, but the adjacent vertebra remains still or moves only slightly, resulting in the movement of the reference member within the carriage, relative to the force transmitter. In this embodiment, the displacement sensor in the device is arranged to measure this movement of the reference member, thus measuring the relative movement of the reference member to the force transmitter and hence the relative movement of the first vertebra (being pushed down by the force transmitter) and the adjacent vertebra on which the reference member sits. Such embodiment allows for different configuration of the gripping portion and housing and a more rigid connection between the two, and in some embodiments the gripping portion forms part of the housing. Support feet in such configuration are movably connected to the frame and/or housing, such that they do not exert any substantial force on the back of the patient as force is applied to the gripping portion.

In another embodiment, as illustrated in FIGS. 9-11 and 15, the reference member is fixed to the housing and the displacement sensor is arranged to measure the displacement of the force transmitter relative to the housing/reference member.

The displacement sensor can in this embodiment be a linear encoder measuring the displacement of the force transmitter or of a displacement member that moves with the distal end of the force transmitter.

The housing may be engaged to the frame or engaged with an adjustable portion of the frame, through a rotation axis, which axis lies horizontally and orthogonal to the spine, when the device is placed on the back of a subject for measurement. Thus, the angle of the force transmitter and gripping means with respect to the spine can be adjusted, and the force transmitter can be adjusted to be essentially orthogonal to the spinal axis at the vertebra under the force transmitter, In some useful embodiments, the housing is slidably engaged to the support frame, such that the housing, with the engaged gripping means and force transmitter, can be moved along the frame but preferably such that the housing can then be locked in a certain position on the support frame, This can make it easier to measure mobility of vertebrae when the curvatures of the spine are large.

The support frame can be formed in various ways. It should preferably be shaped so as to keep the device stable on the back of the subject while force is applied. The support frame can thus suitably be shaped such that it rests on both sides of the spine such as e.g. by a pair of members lying in the direction of the spine, each on one side, or supporting feet, resting on the back of the subject, which can suitably be two, three or four. The reference member is in some embodiments arranged to function as a central supporting foot.

In certain embodiments, the housing and support frame are arranged such that at least a portion of the housing can be rotated around a part of the frame that supports the force transmitter, such that the support feet be arranged on the opposite side the reference member. This way, the device can be used on vertebrae further down on the spine even when the lumbar curve shows excessive curvature.

Figure 1:
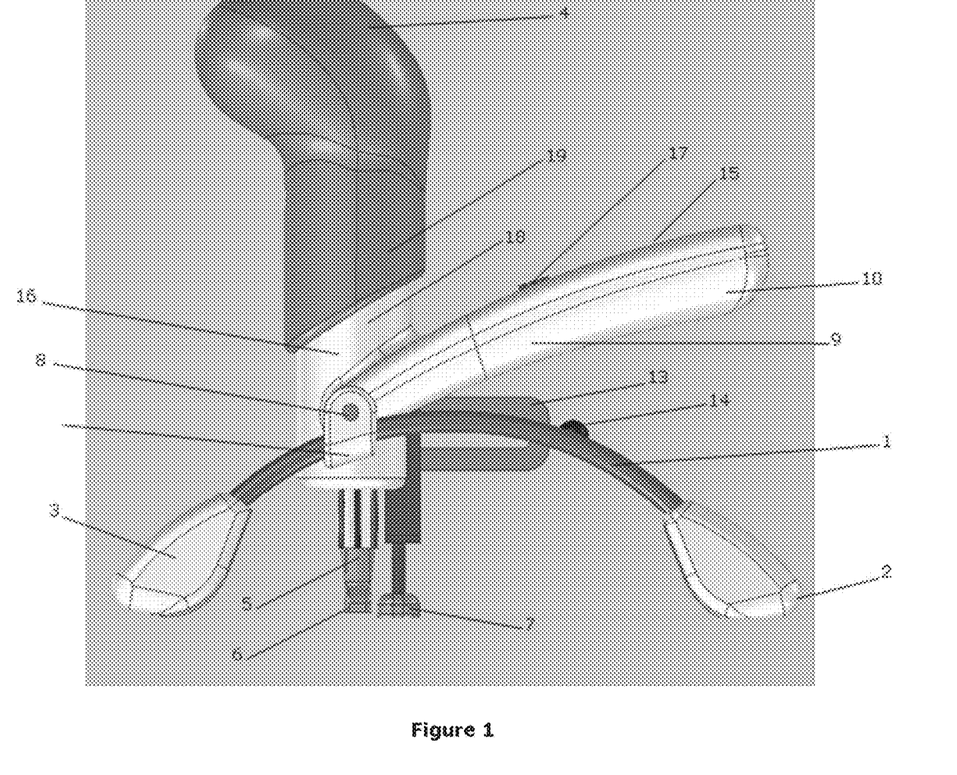
FIG. 1: Side view of one embodiment of the device.
Figure 5:
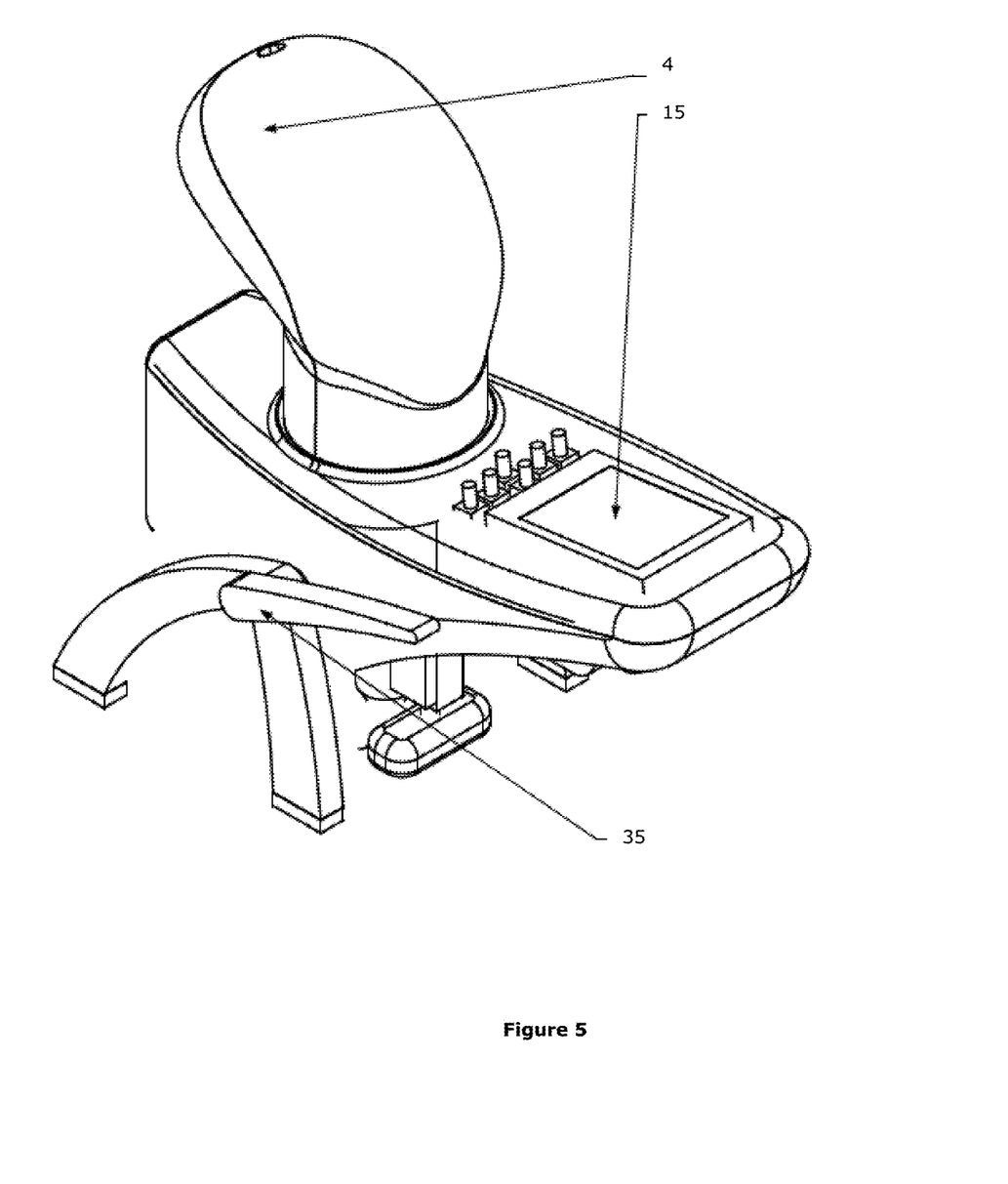
FIG. 5: Alternative compact embodiment with a different support frame.
Figure 6:
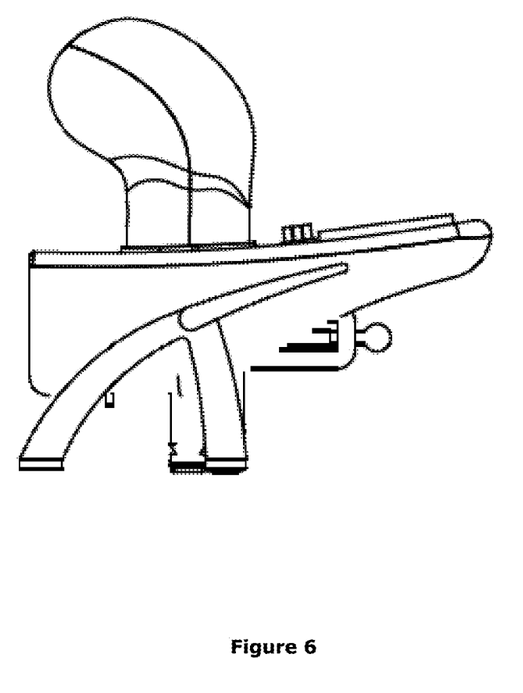
FIG. 6: Embodiment from FIG. 5, showing side view.
Figure 7:
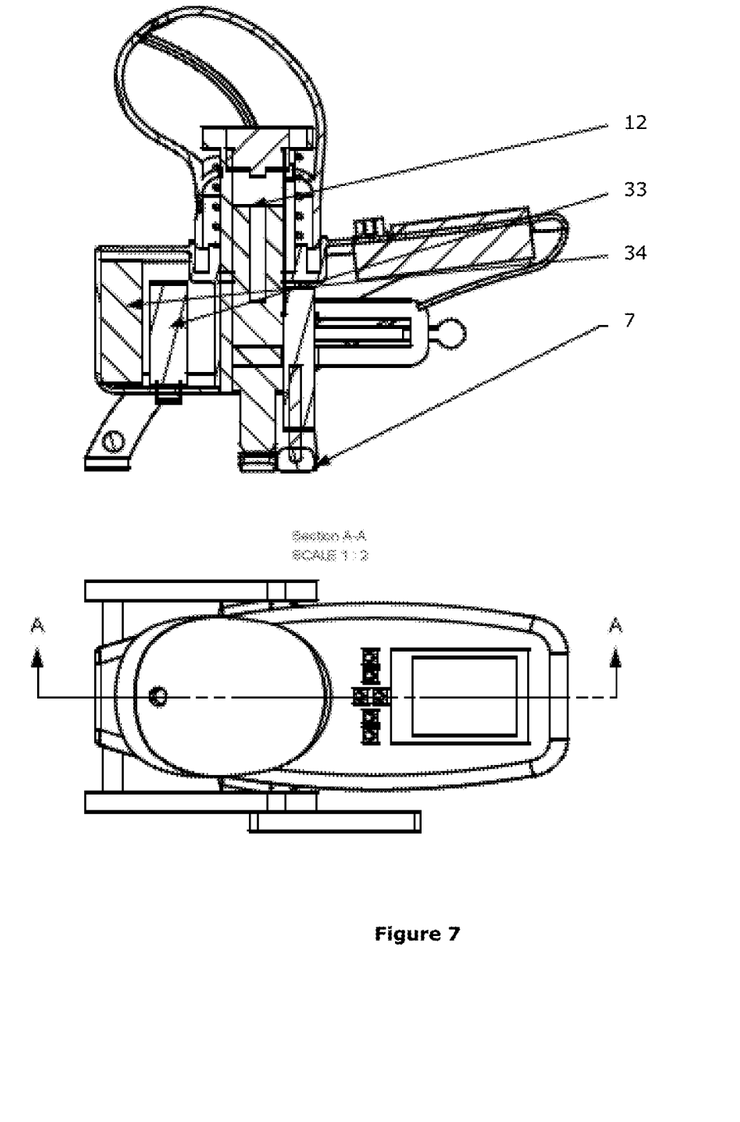
FIG. 7: Embodiment from FIGS. 5 and 6, showing cross-section and top view.
Figure 8:
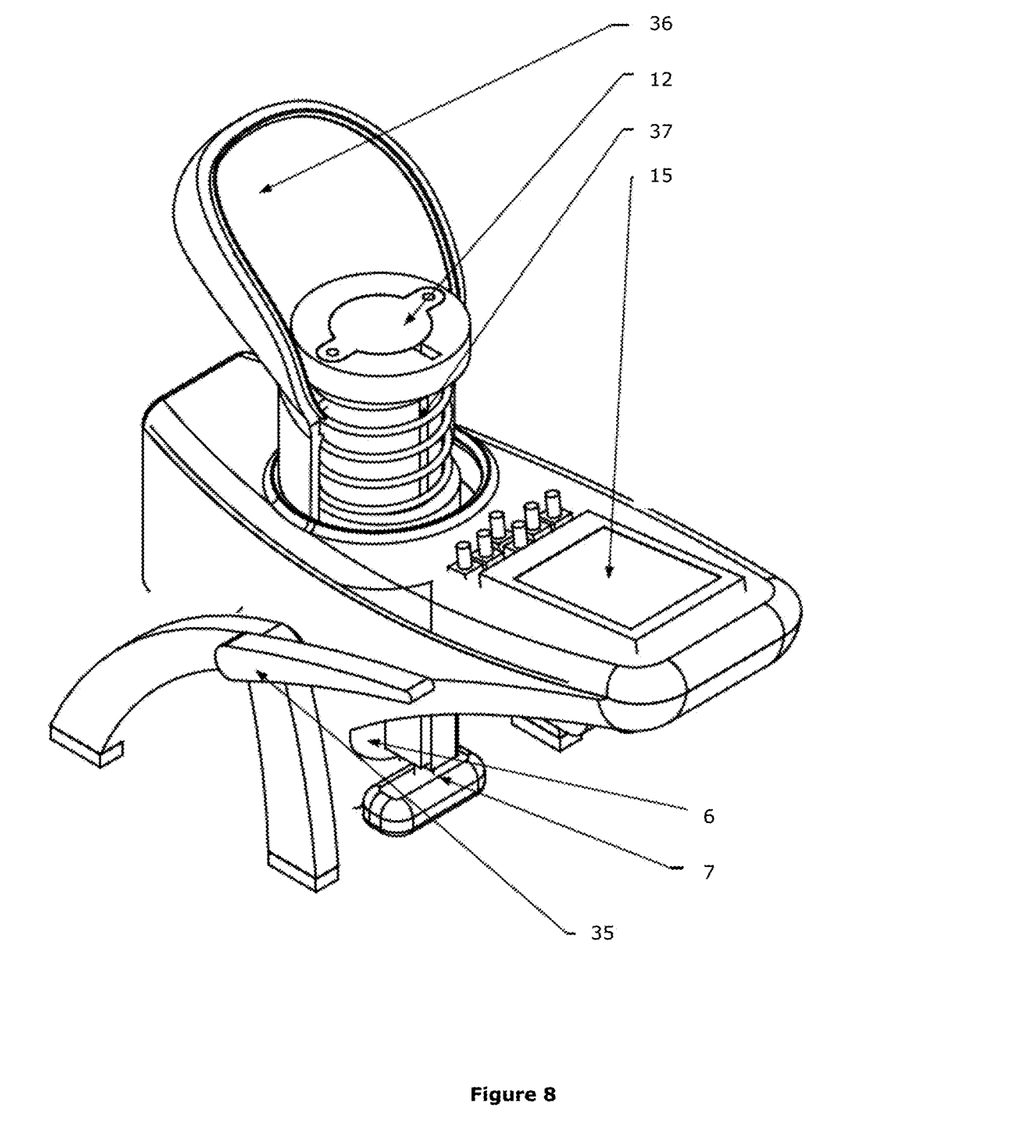
FIG. 8: View after opening gripping portion.

A useful embodiment is illustrated in FIG. 1, a housing 9 forms part of the frame, the housing having adjustably connected to it on each side of the housing arch-like support feet 2,3 that rest on each side of the spine, when the device is in use. The position of the support feet relative to the housing can be adjusted to adjust the orientation of the device, which is preferably such that the force transmitter 5 is oriented orthogonal to the spinal axis within the vertebra to be measured. FIGS. 5-7 show a similar embodiment with more compact support feet joined to the housing adjustably, having an adjustment lever 35 to loosen and adjust the position of the support feet.

Figure 9:
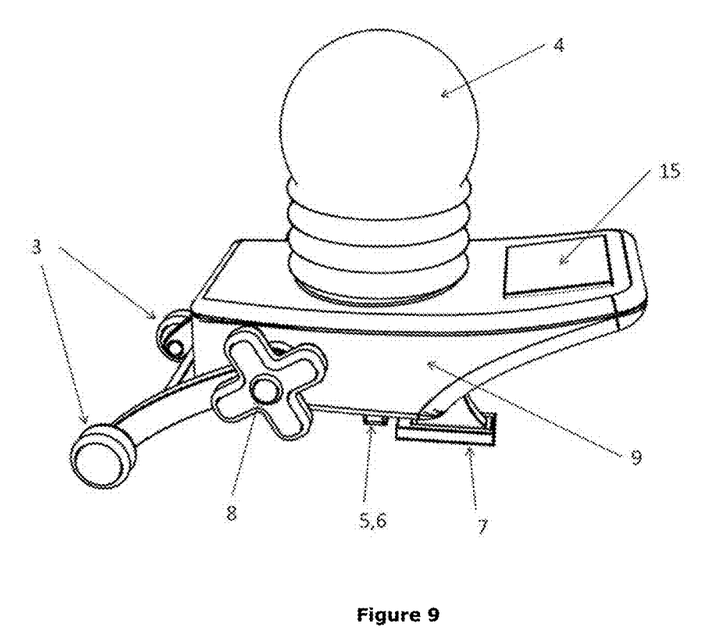
FIG. 9: Perspective view of another embodiment, with fixed reference member.
Figure 10:
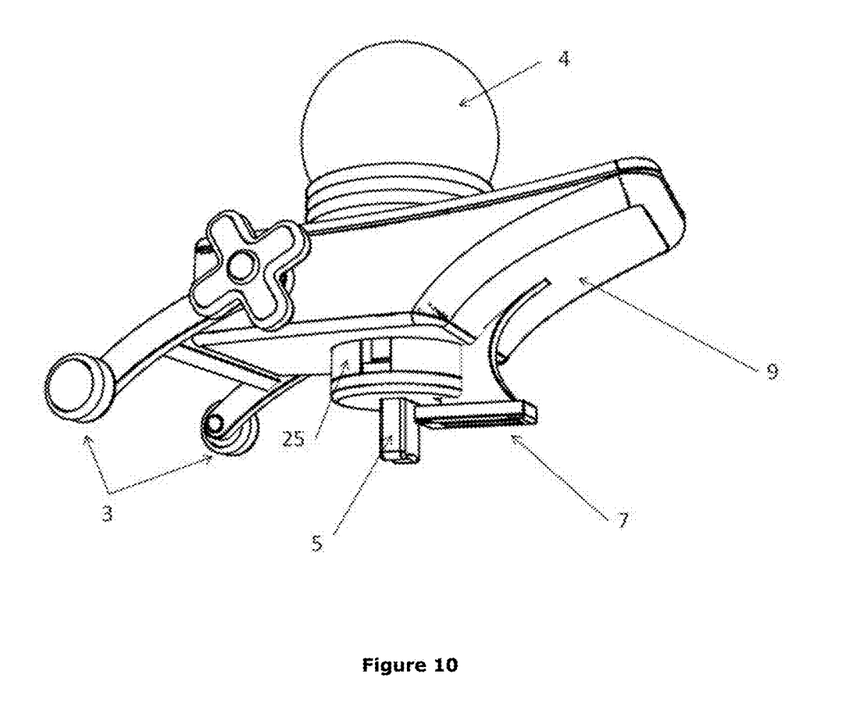
FIG. 10: bottom view of embodiment from FIG. 9.
Figure 11:
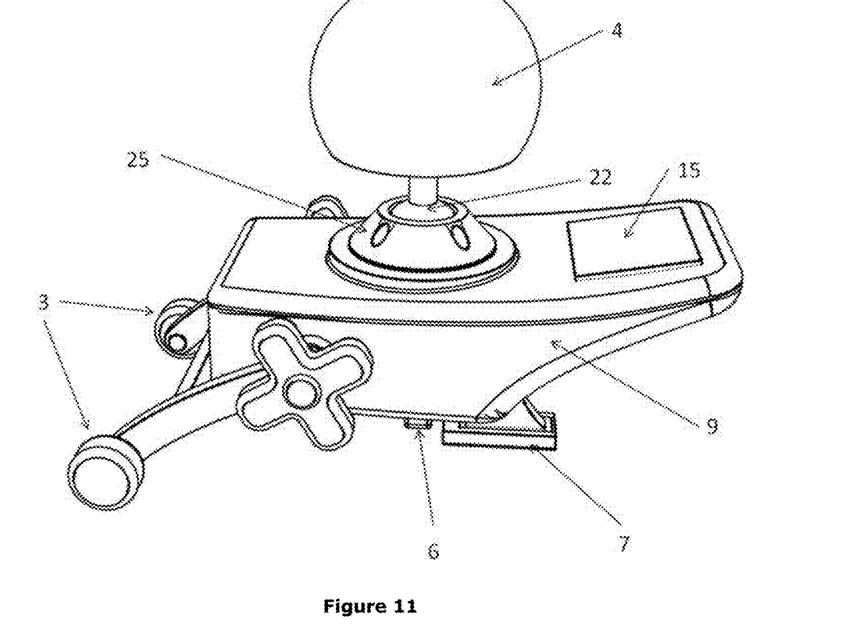
FIG. 11: Another embodiment, with different gripping portion, without enclosing cap.

Another embodiment is shown in FIGS. 9-11, where a housing forms part of the frame, having a pair of adjustable support feet 3 and the reference member 7 acting as a central support foot, i.e. a total of three support feet.

The support frame can in some embodiments comprise transverse supporting beams that lie across the spine, preferably such, though, that they do not interfere with protruding vertebra, e.g. by having gaps or bends in their centre such they rest on each side of the spine. The frame provides stability when force is applied to the gripping portion, this is important as the force in conventional spinal mobility measurements can be in the range of 10-200 N (1-20 kg) such as in the range of 10-100 N (1-10 kg).

In useful embodiments the device further comprises a data output means in the form of a display 15 (e.g. liquid crystal type), for presenting data and informing the practitioner about the measurements. The device can further comprise a data output port 33 and actuators for initiating and controlling measurements.

The electrical power source for the device of the present invention can be a battery 34 or an electrical cord connecting the device to an external power source. Batteries for the device can be conventional single-use batteries or chargeable batteries, in a useful embodiment the battery is charged when the device is placed in a docking station, or the battery compartment can be removed from the device and placed in a charging dock, or alternatively the device is docketed through a cable or cord to a power supply. A docking arrangement with a docking station or cord can also be used to transmit collected data from the device to a computer, for further processing and analysis.

The data output means of the present invention can be either or both an interface for manual/visual readout or a data output port 33. An interface can be a display component 15 such as a liquid crystal display, which outputs data indicating the status of a measurement or a result of a particular measurement. A data output port can be adapted for any data transfer plug such as but not limited to USB, fire wire, 8P8C, or DE-9 connectors.

The device of the present invention can in some embodiments comprise a data storage means, such as a small memory device for storing data from measurements. Such data is then stored in the device and then preferably transferred into a computer through the data output means.

The device can further comprise an actuator for initiating measurements. Such actuators can be a simple on-off switch, but also touch-sensitive actuators for browsing between programs or individual measurements stored in the device.

In an embodiment of the present invention the device further comprises a printed circuit board (PCB) to connect all the electrical elements of the device and/or a central processing means (cpu means) for coordinating measurements and data collection. The device of the present invention may further preferably comprise a data output means for transporting data from the device to a data storage means or a computer. In electronics, printed circuit boards are used to mechanically support and electrically connect electronic components using conductive pathways, or traces, etched from copper sheets laminated onto a non-conductive substrate. Alternative names are printed wiring board (PWB), and etched wiring board. Populating the board with electronic components forms a printed circuit assembly (PCA), also known as a printed circuit board assembly (PCBA). PCBs are rugged, inexpensive, and can be highly reliable. They require much more layout effort and higher initial cost than either wire-wrapped or point-to-point constructed circuits, but are much cheaper, faster, and consistent in high volume production. Much of the electronics industry's PCB design, assembly, and quality control needs are set by standards that are published by the IPC organization.

The force is applied on the gripping portion, it is therefore preferred that the gripping portion is ergonomically designed to allow comfortably manual force to be applied. The force should be applied substantially vertically in relation to the axis of the spine at the point of the vertebra being measured. However, as the spine is not straight, it is preferred that the angle of the load sensor and gripping portion can be adjusted such that the force transmitter is directed vertically (orthogonally) with respect to the spine. This can be achieved by connecting the force transmitter and gripping portion on the frame with a rotational axis, which lies horizontally and orthogonal to the spine when the device is mounted. Preferably, the rotational motion can be blocked, by locking the angle of the load sensor, to prevent unintentional tilting of the sensor during measurement.

Detailed Description Of Embodiments

Illustrative embodiments of the invention will be described in more detail with reference to the drawings. FIG. 1 shows a side view of a device according to the invention. The frame 1 comprises two-arch like side bars 1 (one is seen), the ends of which form support feet 2,3. An axis 8 joins a main housing 9 to the frame arch members 1. The force transmitter 5 extends downwardly from the housing, as does an adjacent reference member 7, which is connected to the device through a carriage 13, allowing adjustment of the distance between the force transmitter and the reference member. The knob 14 is for adjusting the position of the reference member along the carriage 13. The carriage 13 is joined to and moves with the portion of the device that moves vertically with the force transmitter. Thus, the support for the reference member moves vertically along with the force transmitter. The reference member 7, however, moves slidably and essentially frictionless within the support, and thus its movement is used to measure the relative movement of the force transmitter, as it pushes down a first vertebra while the reference member is located on an adjacent vertebra. A displacement sensor (not shown) within the device is used to measure the displacement of the reference member. The gripping portion 4 extends above the housing, along the axis of the force transmitter, such that a force can be applied on the gripping portion 4, being transmitted vertically in the direction of the force transmitter 5. This is achieved by slidably engaging the gripping portion to the housing through the lower end 19 of the gripping portion forming a collar region sliding along a tubular member of the central portion 16 of the housing 9. Inside the tubular member is the connection between the gripping member and force transmitter. The housing 9 is designed to accommodate a battery compartment and an extending display portion 10 having a display 15. An input interface is included in the form of buttons 17.

The batteries can either be single use batteries or chargeable, preferably a built-in battery chargeable by placing the device in a charging docking station (not shown) or through a cord (e.g. USB connection that carries a charging voltage). A load cell (not shown) is placed in the housing (within central portion 16) connected to the force transmitter 5. The force transmitter is extended to a ergonomically shaped head 6, which is made from rigid material and applies pressure onto a vertebra when the device is placed onto the spine and force applied to the force transmitter by manually pressing downwardly on the gripping portion.

Figure 2:
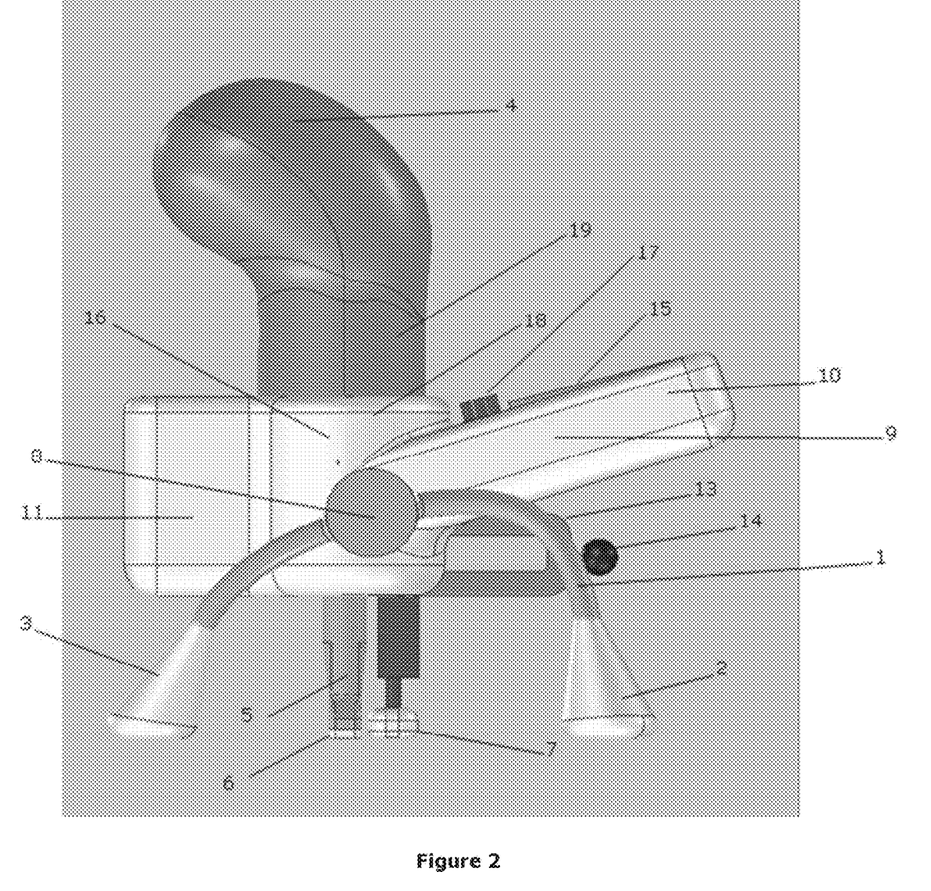
FIG. 2: Side view of a related embodiment of the device.

FIG. 2 shows a related embodiment where the frame is more compact than in the version of FIG. 1. This has the advantage that the device more readily can be used on vertebrae closer to the neck region. The main housing 9 is made more compact by moving the battery compartment 11 opposite to the central portion 16. The lower end 19 of the gripping portion 4 slides inside a suitable shaped receiving area of the central portion 16 of the housing 9 in this embodiment.

Figure 3:
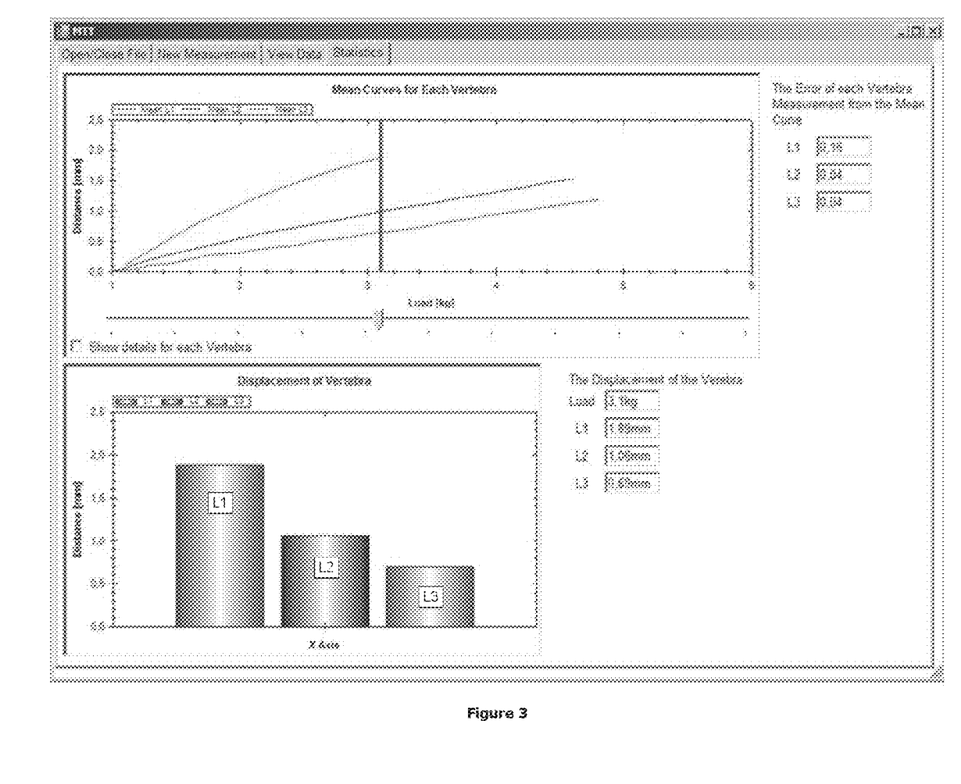
FIG. 3: Screen view from a program for viewing and analysing the output from a device of the invention.

FIG. 3 shows the output from a device of the invention, a screen view as presented in a dedicated program which imports data from the device for further analysis and graphical representation. The upper panel of the figure shows results of three different vertebras, the displacement in mm on the Y-axis as a function of the load (in Newton) on the X-axis. The lower panel shows a diagram illustrating the different displacement of the three vertebrae at a certain load (3.1 kg; the load at the vertical line across the spectrum in the upper panel).

Figure 4:
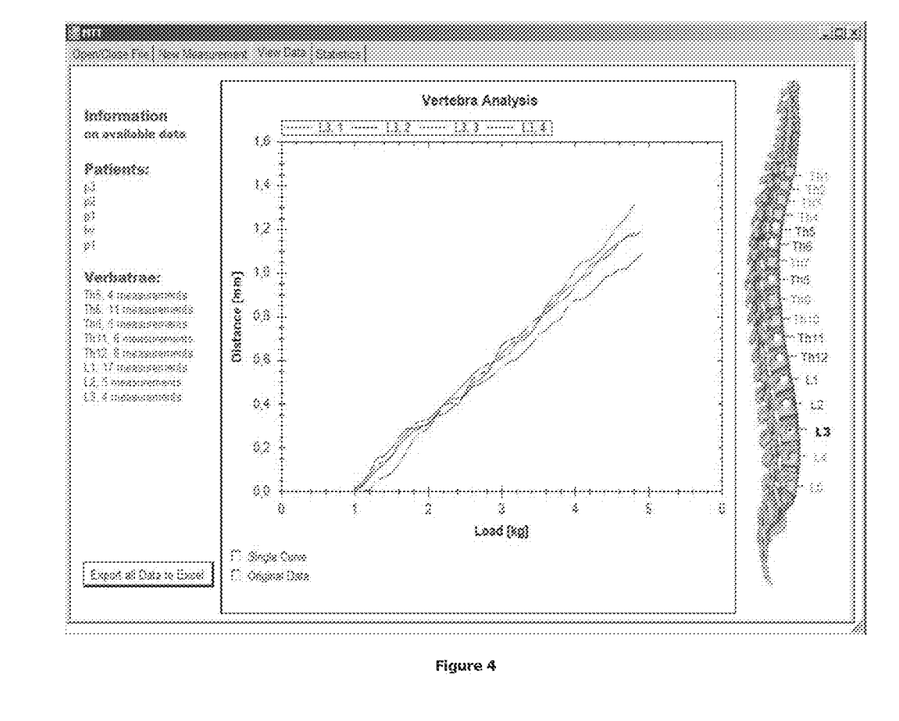
FIG. 4: Another screen view from an output analysis program

FIG. 4 shows a different output from the same program, and shows similar displacement-load curves, for four measurements of the same vertebra in a subject. The program can then calculate the mean curve based on these four individual measurements. The slope of the measured curves provide an indication of the spinal mobility.

The device data output means of the device can suitably include a port at the aft end of the device (not shown). The data output means can be either a socket for a cord/cable or a wireless transceiver for communicating data from the device into a printer or a computer. An electrical contact is also provided, which is either a contact fitting a recharging docking device or for an electrical cord connected to a power supply.

The display portion of the apparatus illustrated in FIG. 1 has an LCD-screen 15 and a switch which is one of the buttons 17. The switch can either be an on/off switch or a switch to initiate a measurement.

FIGS. 5-8 illustrates an alternative but technically equivalent embodiment of the device shown in FIGS. 1 and 2. This alternative device is more compact and has a pair of support feet 2,3, a reference member 7 and force transmitter 5 with a force transmitter head 6.

FIG. 9 introduces a slightly different embodiment. The frame is simplified and the body housing forms an integral part of the frame. A pair of distal support feet 3 are attached to the housing with an axis 8 and tightening screw, such that they can be rotatably adjusted to allow adjusting the angle of the force transmitter with respect to the spine of the subject. The reference member 7 forms a proximal central support foot which is an integral part of the housing. The force transmitter 5 extends downwardly, adjacent to the reference member. In this embodiment, the displacement sensor is internal and arranged to measure directly the displacement of the force transmitter relative to the reference member/housing. FIG. 10 shows a bottom perspective view, showing the force transmitter extending from a shaft unit 25, the cap of the gripping portion has been removed, to show the ball joint 22 connecting the gripping portion to the device. The ball joint forces the user to apply a force essentially directly downwardly, along the axis of the force transmitter, thus preventing the user from exerting lateral forces. The display 15 is in some embodiments a touch screen.

Figure 12:
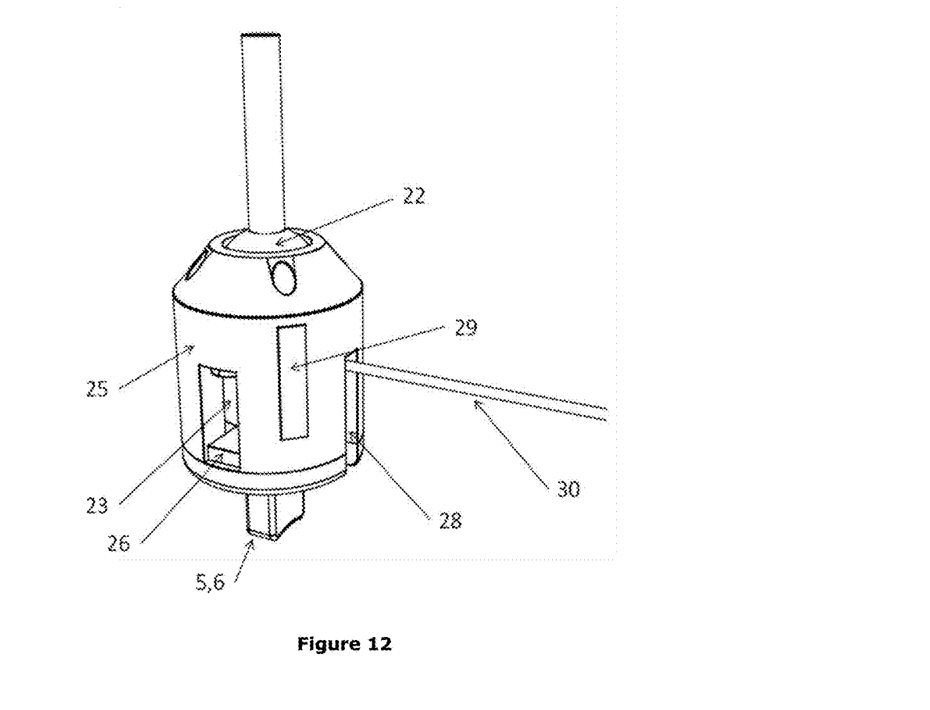
FIG. 12: Internal portion of housing, showing connection between gripping portion and force transmitter.

A shaft unit 25 connects the force transmitter and gripping portion. The shaft unit is depicted in FIG. 12 and in a blow-up view in FIG. 13. The shaft unit comprises the ball joint 22 in contact with a load cell 23, arranged to come in contact with the force transmitter 5, such that force from the gripping portion is transmitted to the force transmitter, and measured by the load cell.

Figure 13:
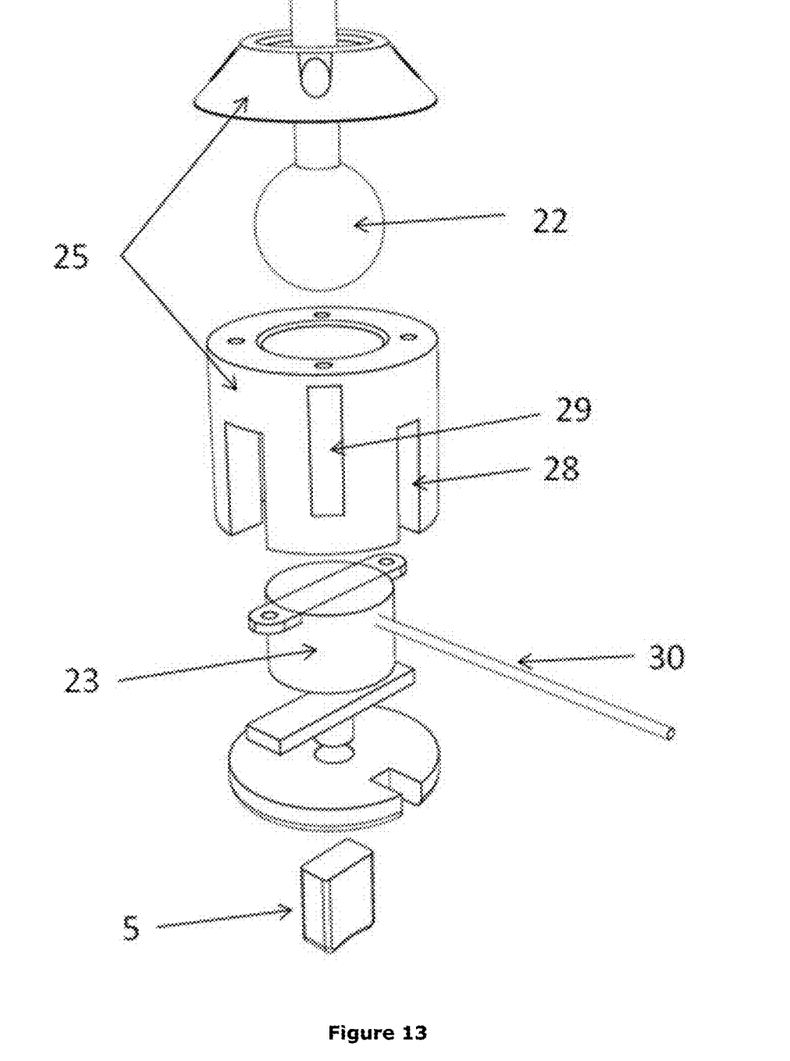
FIG. 13: Blow-up view of portion from FIG. 12.

A linear encoder is used in this embodiment as displacement sensor. The shaft unit 25 comprises a magnetic strip 29 and a linear encoder sensor (e.g. AS5306 from Austria Microsystems) is arranged within the housing to detect movement of the strip.

Figure 14:
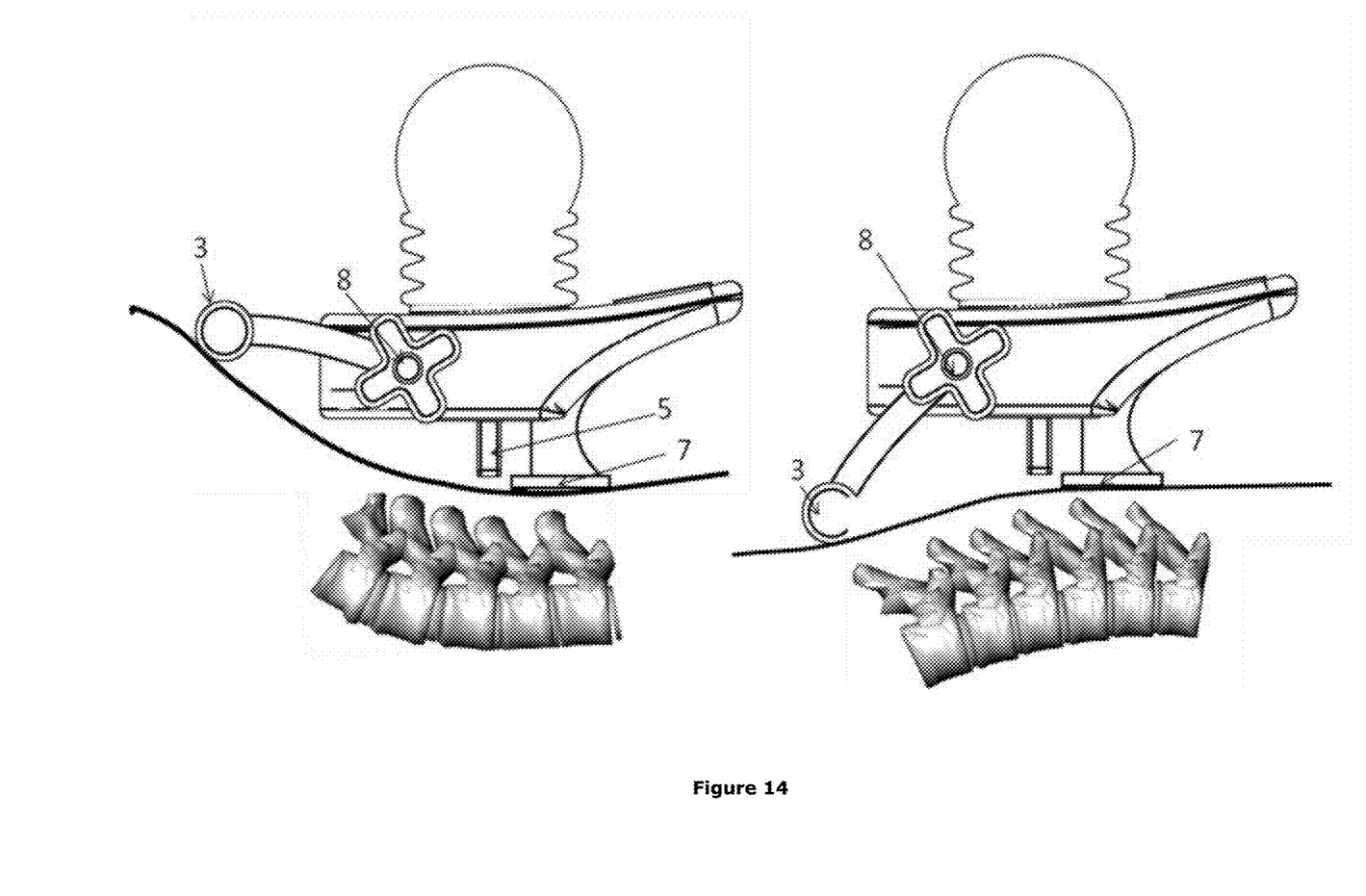
FIG. 14: Illustration showing adjustment of support feet to adjust proper orientation of the force transmitter.
Figure 15:
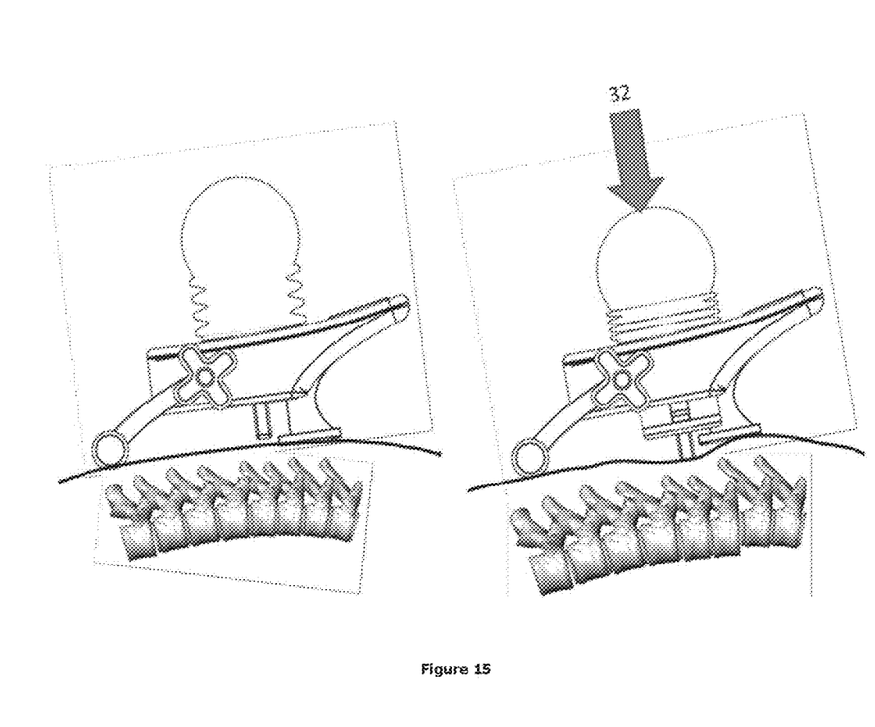
FIG. 15: Illustration showing action of device, where a force is applied to the gripping means to press down the force transmitter.

FIG. 14 shows operation of the device from FIGS. 9-11, illustrating how the angle of the support feet 3 is adjusted by rotation around the axis 8, in order to maintain a correct essentially vertical orientation of the force transmitter with respect to the spinal axis, at the vertebra being measured. FIG. 15 shows how the force transmitter is pushed down and displaces a vertebra when a force 32 is exerted on the gripping portion.

The invention claimed is:

1. A method for measuring spinal mobility of a human subject, the method comprising the steps of:
    a) placing a device on the spine of the human subject, the device comprising a support frame comprising support feet, a force transmitter and a reference member, said frame supporting a gripping means engaged with the force transmitter, and a reference displacement sensor, such that, when in use, the force transmitter is positioned on a first vertebra, and the reference member rests on a vertebra to said first vertebra,
    b) applying a force substantially perpendicular to the spinal axis in said first vertebra to the gripping portion of the device and thereby pressure to said first vertebra through the force transmitter,
    c) measuring by means of the reference displacement sensor the displacement of the force transmitter relative to the adjacent vertebra,
    d) measuring the applied force by means of a load cell within said device connected to said force transmitter, wherein said displacement as a function of the applied force provides an indication of spinal mobility.

2. The method according to claim 1, wherein steps b) and c) are repeated for at least two vertebrae.

3. The method according to claim 1, wherein said force is applied manually.

4. The method of claim 1, further comprising collecting data representing said displacement and providing an output based on said data, indicating said spinal mobility.

\* \* \* \* \*